(12) United States Patent
Ichinohe et al.

(10) Patent No.: US 8,545,512 B2
(45) Date of Patent: Oct. 1, 2013

(54) INTRAOCULAR LENS INSERTION DEVICE

(75) Inventors: Takashi Ichinohe, Tokyo (JP);
Kazunori Kudoh, Tokyo (JP)

(73) Assignee: Hoya Corporation, Tokyo (JP)

( * ) Notice: Subject to any disclaimer, the term of this patent is extended or adjusted under 35 U.S.C. 154(b) by 242 days.

(21) Appl. No.: 11/814,508

(22) PCT Filed: Jan. 11, 2006

(86) PCT No.: PCT/JP2006/300217
§ 371 (c)(1),
(2), (4) Date: Jul. 23, 2007

(87) PCT Pub. No.: WO2006/080191
PCT Pub. Date: Aug. 3, 2006

(65) Prior Publication Data
US 2009/0043313 A1    Feb. 12, 2009

(30) Foreign Application Priority Data

Jan. 26, 2005   (JP) .................................. 2005-018850

(51) Int. Cl.
*A61F 9/00* (2006.01)
(52) U.S. Cl.
USPC ............................ 606/107; 604/218; 604/220
(58) Field of Classification Search
USPC ................. 606/107, 6.12, 167, 185; 604/187, 604/218, 220
See application file for complete search history.

(56) References Cited

U.S. PATENT DOCUMENTS

| | | | |
|---|---|---|---|
| 2,761,446 | A | 9/1956 | Reed |
| 4,205,747 | A | 6/1980 | Gilliam et al. |
| 4,269,307 | A | 5/1981 | LaHaye |
| 4,423,809 | A | 1/1984 | Mazzocco |
| 4,573,998 | A | 3/1986 | Mazzocco |
| 4,608,049 | A | 8/1986 | Kelman |
| 4,634,423 | A | 1/1987 | Bailey |
| 4,681,102 | A | 7/1987 | Bartell |
| 4,697,697 | A | 10/1987 | Graham et al. |
| 4,699,140 | A | 10/1987 | Holmes |
| 4,702,244 | A | 10/1987 | Mazzocco |
| 4,715,373 | A | 12/1987 | Mazzocco et al. |
| 4,747,404 | A | 5/1988 | Jampel et al. |

(Continued)

FOREIGN PATENT DOCUMENTS

| | | |
|---|---|---|
| DE | 3610925 | 10/1987 |
| DE | 4110278 | 10/1992 |

(Continued)

*Primary Examiner* — Katherine Dowe
*Assistant Examiner* — Katrina Stransky
(74) *Attorney, Agent, or Firm* — Henricks, Slavin & Holmes LLP

(57) ABSTRACT

An intraocular insertion device capable of safely performing discharge operation of a lens by a simpler construction. The intraocular lens insertion device has a body provided with a lens placement section where the lens is placed and a tube section for inserting the lens into an eye and has a plunger for discharging the lens placed on the lens placement section. The lens placement section has an upper holding member and a lower holding member. The upper holding member has a rib projecting on advancement axis A, to the lower side of the lens placement section. The lower holding member has a U-shaped cross-section and is constituted of a left and right pair of uprising sections and a pressing section uniting the uprising sections at their lower ends.

22 Claims, 5 Drawing Sheets

(56) References Cited

U.S. PATENT DOCUMENTS

| | | |
|---|---|---|
| 4,750,498 A | 6/1988 | Graham |
| 4,759,359 A | 7/1988 | Willis et al. |
| 4,763,650 A | 8/1988 | Hauser |
| 4,765,329 A | 8/1988 | Cumming et al. |
| 4,769,034 A | 9/1988 | Poley |
| 4,781,719 A | 11/1988 | Kelman |
| 4,787,904 A | 11/1988 | Severin |
| 4,819,631 A | 4/1989 | Poley |
| 4,834,094 A | 5/1989 | Patton |
| 4,862,885 A | 9/1989 | Cumming |
| 4,880,000 A | 11/1989 | Holmes et al. |
| 4,919,130 A | 4/1990 | Stoy et al. |
| 4,934,363 A | 6/1990 | Smith et al. |
| 4,955,889 A | 9/1990 | Van Gent |
| 4,976,716 A | 12/1990 | Cumming |
| 4,988,352 A | 1/1991 | Poley |
| 4,994,028 A | 2/1991 | Leonard et al. |
| 5,066,297 A | 11/1991 | Cumming |
| 5,098,439 A | 3/1992 | Hill et al. |
| 5,123,905 A | 6/1992 | Kelman |
| 5,139,501 A | 8/1992 | Klaas |
| 5,171,241 A | 12/1992 | Buboltz et al. |
| 5,176,686 A | 1/1993 | Poley |
| 5,190,552 A | 3/1993 | Kelman |
| 5,190,553 A | 3/1993 | Kanert et al. |
| 5,222,972 A | 6/1993 | Hill et al. |
| 5,242,450 A | 9/1993 | McDonald |
| 5,259,395 A | 11/1993 | Li |
| 5,275,604 A | 1/1994 | Rheinish et al. |
| 5,281,227 A | 1/1994 | Sussman |
| 5,304,182 A | 4/1994 | Rheinish et al. |
| 5,354,333 A | 10/1994 | Kammann et al. |
| 5,395,378 A | 3/1995 | McDonald |
| 5,425,734 A | 6/1995 | Blake |
| 5,454,818 A | 10/1995 | Hambleton et al. |
| 5,468,246 A | 11/1995 | Blake |
| 5,474,562 A | 12/1995 | Orchowski et al. |
| 5,494,484 A | 2/1996 | Feingold |
| 5,496,328 A | 3/1996 | Nakajima et al. |
| 5,499,987 A | 3/1996 | Feingold |
| 5,562,676 A | 10/1996 | Brady et al. |
| 5,571,113 A | 11/1996 | McDonald |
| 5,578,042 A | 11/1996 | Cumming |
| 5,582,613 A | 12/1996 | Brady |
| 5,582,614 A | 12/1996 | Feingold |
| 5,584,304 A | 12/1996 | Brady |
| 5,616,148 A | 4/1997 | Eagles et al. |
| 5,620,450 A | 4/1997 | Eagles et al. |
| 5,643,275 A | 7/1997 | Blake |
| 5,643,276 A | 7/1997 | Zaleski |
| 5,645,534 A | 7/1997 | Chanoch |
| 5,653,715 A | 8/1997 | Reich et al. |
| 5,653,753 A | 8/1997 | Brady et al. |
| 5,702,402 A | 12/1997 | Brady |
| 5,702,441 A | 12/1997 | Zhou |
| 5,716,364 A | 2/1998 | Makker et al. |
| 5,728,075 A | 3/1998 | Levander |
| 5,728,102 A | 3/1998 | Feingold et al. |
| 5,735,858 A | 4/1998 | Makker et al. |
| 5,766,181 A | 6/1998 | Chambers et al. |
| 5,772,666 A | 6/1998 | Feingold et al. |
| 5,772,667 A | 6/1998 | Blake |
| 5,776,138 A | 7/1998 | Vidal et al. |
| 5,800,442 A | 9/1998 | Wolf et al. |
| 5,803,925 A | 9/1998 | Yang et al. |
| 5,807,400 A | 9/1998 | Chambers et al. |
| 5,810,833 A | 9/1998 | Brady et al. |
| 5,810,834 A | 9/1998 | Heyman |
| 5,860,984 A | 1/1999 | Chambers et al. |
| 5,860,986 A | 1/1999 | Reich et al. |
| 5,868,751 A | 2/1999 | Feingold |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,891,152 A | 4/1999 | Feingold |
| 5,902,307 A | 5/1999 | Feingold et al. |
| 5,919,197 A | 7/1999 | McDonald |
| 5,921,989 A | 7/1999 | Deacon et al. |
| 5,928,245 A | 7/1999 | Wolf et al. |
| 5,941,886 A | 8/1999 | Feingold |
| 5,942,277 A | 8/1999 | Makker et al. |
| 5,944,725 A | 8/1999 | Cicenas |
| 5,947,974 A | 9/1999 | Brady et al. |
| 5,947,975 A | 9/1999 | Kikuchi et al. |
| 5,957,748 A | 9/1999 | Ichiha |
| 6,001,107 A | 12/1999 | Feingold |
| 6,010,510 A | 1/2000 | Brown et al. |
| 6,022,358 A | 2/2000 | Wolf et al. |
| 6,048,348 A | 4/2000 | Chambers et al. |
| 6,051,000 A | 4/2000 | Heyman |
| 6,056,757 A | 5/2000 | Feingold et al. |
| 6,056,758 A | 5/2000 | Vidal et al. |
| 6,059,791 A | 5/2000 | Chambers |
| 6,074,397 A | 6/2000 | Chambers et al. |
| 6,083,230 A | 7/2000 | Makker et al. |
| 6,093,193 A | 7/2000 | Makker et al. |
| 6,129,733 A | 10/2000 | Brady et al. |
| 6,142,999 A | 11/2000 | Brady et al. |
| 6,143,000 A | 11/2000 | Feingold |
| 6,162,229 A | 12/2000 | Feingold et al. |
| 6,174,315 B1 | 1/2001 | Chambers et al. |
| 6,214,015 B1 | 4/2001 | Reich et al. |
| 6,241,737 B1 | 6/2001 | Feingold |
| 6,248,111 B1 | 6/2001 | Glick et al. |
| 6,251,114 B1 | 6/2001 | Farmer et al. |
| 6,254,607 B1 | 7/2001 | Makker et al. |
| 6,267,768 B1 | 7/2001 | Deacon |
| 6,283,975 B1 | 9/2001 | Glick et al. |
| 6,283,976 B1 | 9/2001 | Portney |
| 6,312,433 B1 | 11/2001 | Butts |
| 6,334,862 B1 | 1/2002 | Vidal et al. |
| 6,336,932 B1 | 1/2002 | Figueroa et al. |
| 6,355,046 B2 | 3/2002 | Kikuchi et al. |
| 6,371,960 B2 | 4/2002 | Heyman et al. |
| 6,386,357 B1 | 5/2002 | Egawa |
| 6,387,101 B1 | 5/2002 | Butts et al. |
| 6,398,788 B1 | 6/2002 | Makker et al. |
| 6,406,481 B2 | 6/2002 | Feingold et al. |
| 6,428,545 B2 | 8/2002 | Portney |
| 6,447,519 B1 | 9/2002 | Brady et al. |
| 6,447,520 B1 | 9/2002 | Ott et al. |
| 6,468,282 B2 * | 10/2002 | Kikuchi et al. ............ 606/107 |
| 6,471,708 B2 | 10/2002 | Green |
| 6,491,697 B1 | 12/2002 | Clark et al. |
| 6,497,708 B1 | 12/2002 | Cumming |
| 6,500,181 B1 * | 12/2002 | Portney ........................ 606/107 |
| 6,506,195 B2 | 1/2003 | Chambers et al. |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,607,537 B1 * | 8/2003 | Binder ........................ 606/107 |
| 6,629,979 B1 | 10/2003 | Feingold |
| 6,666,871 B2 | 12/2003 | Kikuchi et al. |
| 6,679,891 B2 | 1/2004 | Makker et al. |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas et al. |
| 6,793,674 B2 | 9/2004 | Zapata |
| 6,858,033 B2 | 2/2005 | Kobayashi |
| 6,921,405 B2 | 7/2005 | Feingold et al. |
| 6,923,815 B2 | 8/2005 | Brady et al. |
| 6,976,989 B1 | 12/2005 | Vincent |
| 7,014,641 B2 * | 3/2006 | Kobayashi et al. ........... 606/107 |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |

| | | | | | |
|---|---|---|---|---|---|
| 7,348,038 B2 | 3/2008 | Makker et al. | | FOREIGN PATENT DOCUMENTS | |
| 7,422,604 B2 | 9/2008 | Vaquero et al. | | | |
| 7,429,263 B2 | 9/2008 | Vaquero et al. | EP | 0363213 | 4/1990 |
| 7,458,976 B2 | 12/2008 | Peterson et al. | EP | 0727966 | 9/2003 |
| 7,476,230 B2 | 1/2009 | Ohno et al. | EP | 1832247 A1 | 9/2007 |
| 7,494,505 B2 | 2/2009 | Kappelhof et al. | EP | 1338254 | 12/2008 |
| 7,645,300 B2 | 1/2010 | Tsai | FR | 2749752 A | 12/1997 |
| 8,273,122 B2 | 9/2012 | Anderson | JP | 63-197453 A | 8/1988 |
| 8,382,769 B2 | 2/2013 | Inoue | JP | 4-212350 A | 8/1992 |
| 8,460,311 B2 | 6/2013 | Ishii | JP | 5-103808 | 4/1993 |
| 8,470,032 B2 | 6/2013 | Inoue et al. | JP | 5-103809 | 4/1993 |
| 8,475,528 B2 | 7/2013 | Ichinohe et al. | JP | 8-024282 A | 1/1996 |
| 2001/0007942 A1 | 7/2001 | Kikuchi et al. | JP | 8-505540 | 6/1996 |
| 2002/0103490 A1 | 8/2002 | Brady | JP | 9-506285 A | 6/1997 |
| 2002/0151904 A1 | 10/2002 | Feingold et al. | JP | 11-113939 A | 4/1999 |
| 2002/0165610 A1 | 11/2002 | Wadlaock | JP | 11-506357 A | 6/1999 |
| 2002/0193805 A1 | 12/2002 | Ott et al. | JP | 2000-516487 A | 12/2000 |
| 2003/0036765 A1 | 2/2003 | Van Noy | JP | 2000-516488 A | 12/2000 |
| 2003/0040755 A1 | 2/2003 | Meyer | JP | 2001-502563 | 2/2001 |
| 2003/0050647 A1 | 3/2003 | Brady | JP | 2001-104347 A | 4/2001 |
| 2003/0088253 A1 | 5/2003 | Seil | JP | 2002-516709 A | 6/2002 |
| 2003/0139749 A1 | 7/2003 | Kikuchi et al. | JP | 2002-355268 A | 12/2002 |
| 2003/0181921 A1* | 9/2003 | Jeannin et al. ............ 606/107 | JP | 2002-541912 A | 12/2002 |
| 2003/0195522 A1 | 10/2003 | McNicholas | JP | 2003-144480 A | 5/2003 |
| 2003/0212406 A1* | 11/2003 | Kobayashi et al. ........ 606/107 | JP | 3412106 B2 | 6/2003 |
| 2003/0212407 A1 | 11/2003 | Kikuchi | JP | 2003-210498 A | 7/2003 |
| 2003/0212409 A1 | 11/2003 | Kobayashi et al. | JP | 2003-325569 A | 11/2003 |
| 2004/0111094 A1 | 6/2004 | Meyer | JP | 2003-325570 A | 11/2003 |
| 2004/0117012 A1 | 6/2004 | Vincent | JP | 2003-325572 A | 11/2003 |
| 2004/0127911 A1* | 7/2004 | Figueroa et al. ........... 606/107 | JP | 2004-024854 A | 1/2004 |
| 2004/0238392 A1 | 12/2004 | Peterson et al. | JP | 2004-188194 A | 7/2004 |
| 2004/0243141 A1 | 12/2004 | Brown et al. | JP | 2004-351196 A | 12/2004 |
| 2005/0033308 A1* | 2/2005 | Callahan et al. ........... 606/107 | JP | 2006-181269 A | 7/2006 |
| 2005/0049605 A1* | 3/2005 | Vaquero et al. ............ 606/107 | JP | 2006-297146 A | 11/2006 |
| 2005/0049606 A1 | 3/2005 | Vaquero et al. | JP | 2006-333924 A | 12/2006 |
| 2005/0125000 A1 | 6/2005 | Tourrette et al. | JP | 2006-333981 A | 12/2006 |
| 2005/0182419 A1 | 8/2005 | Tsai | JP | 2007-503872 A | 3/2007 |
| 2005/0222578 A1 | 10/2005 | Vaquero | JP | 2007-152010 A | 6/2007 |
| 2005/0261703 A1 | 11/2005 | Feingold et al. | JP | 2007-181604 A | 7/2007 |
| 2006/0085013 A1 | 4/2006 | Dusek | JP | 2007-526091 A | 9/2007 |
| 2006/0142781 A1 | 6/2006 | Pynson et al. | JP | 2008-521535 A | 6/2008 |
| 2006/0167466 A1 | 7/2006 | Dusek | JP | 2008-212689 A | 9/2008 |
| 2006/0229633 A1 | 10/2006 | Shepherd | WO | WO9407436 A1 | 4/1994 |
| 2006/0293694 A1 | 12/2006 | Futamura | WO | WO9513022 A1 | 5/1995 |
| 2008/0033449 A1 | 2/2008 | Cole et al. | WO | WO9628122 A1 | 9/1996 |
| 2008/0058830 A1 | 3/2008 | Cole et al. | WO | WO9715253 A1 | 5/1997 |
| 2008/0086146 A1 | 4/2008 | Ishii et al. | WO | WO9812969 A1 | 4/1998 |
| 2008/0097459 A1 | 4/2008 | Kammerlander et al. | WO | 00/45746 A1 | 8/2000 |
| 2008/0221584 A1 | 9/2008 | Downer | WO | WO0062712 A1 | 10/2000 |
| 2009/0036898 A1 | 2/2009 | Ichinohe | WO | WO02071982 A1 | 9/2002 |
| 2009/0112223 A1 | 4/2009 | Downer et al. | WO | WO02096322 A1 | 12/2002 |
| 2009/0125034 A1 | 5/2009 | Pynson | WO | WO2005023154 A1 | 3/2005 |
| 2009/0138022 A1 | 5/2009 | Tu et al. | WO | WO2005070341 A1 | 8/2005 |
| 2009/0204122 A1 | 8/2009 | Ichinohe et al. | WO | WO2005084588 A1 | 9/2005 |
| 2009/0216244 A1 | 8/2009 | Pynson | WO | WO2006070628 A1 | 7/2006 |
| 2009/0248031 A1 | 10/2009 | Ichinohe | WO | WO2006080191 A1 | 8/2006 |
| 2010/0161049 A1 | 6/2010 | Inoue | WO | WO2006090531 A1 | 8/2006 |
| 2010/0185206 A1 | 7/2010 | Ichinohe et al. | WO | WO2007037223 A1 | 4/2007 |
| 2010/0217273 A1 | 8/2010 | Someya et al. | WO | WO2007097221 A1 | 4/2007 |
| 2010/0286704 A1 | 11/2010 | Ichinohe et al. | WO | WO2007080869 A1 | 7/2007 |
| 2011/0082463 A1 | 4/2011 | Inoue | WO | WO2008149794 A1 | 12/2008 |
| 2011/0098717 A1 | 4/2011 | Inoue | WO | WO2008149795 A1 | 12/2008 |
| 2011/0264101 A1 | 10/2011 | Inoue et al. | WO | WO2009058929 A1 | 7/2009 |
| 2011/0270264 A1 | 11/2011 | Shoji et al. | WO | WO2009148091 A1 | 12/2009 |
| 2011/0288557 A1 | 11/2011 | Kudo et al. | WO | WO2011126144 A1 | 10/2011 |
| 2012/0022549 A1 | 1/2012 | Someya et al. | WO | WO2011155636 A1 | 12/2011 |
| 2012/0071887 A1 | 3/2012 | Ichinohe et al. | | | |
| 2013/0006259 A1 | 1/2013 | Sanger | * cited by examiner | | |
| 2013/0018460 A1 | 1/2013 | Anderson | | | |

INTRAOCULAR LENS INSERTION DEVICE

CROSS REFERENCE TO RELATED APPLICATIONS

This is a U.S. national phase application under 35 U.S.C. §371 of International Patent Application No. PCT/JP2006/300217 filed Jan. 11, 2006, which claims priority to Japanese patent application No. 2005-018850, filed Jan. 26, 2005. The International Application was published in Japanese on Aug. 3, 2006 as International Publication No. WO 2006/080191 A1 under PCT Article 21(2). The content of both applications is incorporated herein in its entirety.

FIELD OF THE INVENTION

The present invention relates to an intraocular lens insertion device that inserts an intraocular lens into an aphakic eye after a cataract operation, or, to an intraocular lens insertion device that inserts a phakic intraocular lens during a refractive surgery.

DESCRIPTION OF THE RELATED ART

In cataract operations, the method of removing an opacified lens by phacoemulsification (PEA) and implanting an intraocular lens after the opacified lens has been removed is widely performed. The types of implanting intraocular lens include a hard intraocular lens with an optical area made of a hard material, such as (PMMA), and a soft intraocular lens made of a soft material such as silicone elastomer or soft acrylic resin. When using a hard intraocular lens, the intraocular lens must be inserted through an incision in the cornea or sclera that is of about the same width as the diameter of the optical area but, when using a soft intraocular lens, folding of the optical area allows the intraocular lens to be inserted into the eye through an incision that is smaller than the diameter of the optical area. Further, performing the operation with a smaller incision is desirable because it reduces the risk of post-surgery corneal astigmatism and infection, so there has been a trend in recent years to favor the use of soft intraocular lens. In addition, to insert the lens into the eye, there are cases where a special injector having a long tube through which the lens passes as it is guided into the eye is used. Using such a special intraocular lens injector makes it possible to insert the lens through an incision smaller than 3 mm.

In addition, preset injectors having the lens set in the injector in advance to eliminate the risk of contamination by microbes during lens handling and of possible operational mistakes during lens handling have recently been announced. Some preset injectors are provided with a lens holding mechanism that holds the lens inside the injector in a state that does not stress the optical area and with a lens movement mechanism that moves the lens to a position where it can be pushed out by an discharge device so as to transfer the lens from the lens immovable state during shipment to the lens movable state during use (For example, refer to Japanese Patent Application Laid-Open (JP-A) No. 2003-325570 ("JP '570"), and JP-A No. 2003-325572 ("JP '572")).

SUMMARY OF THE INVENTION

However, a characteristic of the invention disclosed in the above-mentioned JP '570 and JP '572 is that during use the lens must be moved from the holding position to a position from where it can be discharged, and there is concern that problems will occur during the moving operation. In addition, the construction is such that after moving the lens to a position where it can be discharged, the lens is folded while being discharged from a state where the optical area is nearly undeformed, so the movement distance required by the discharge mechanism is long, which creates the problems of trouble occurring during discharge and of the insertion device needing to be large.

In view of the above, an object of the present invention is to provide an intraocular lens insertion device having a simple construction that safely performs the lens discharge operation and solves the afore-mentioned problems.

To achieve the afore-mentioned objective, the present invention according to a first aspect of the invention is an intraocular lens insertion device that is characterized by a body having a lens placement section that holds the lens and a tubular body that guides the lens, and a lens discharge mechanism set in the lens advancement axis, wherein the afore-mentioned lens placement section is provided with a deformation mechanism to having an upper holding member that holds the lens from above along the advancement axis from back to front and a lower holding member that holds both sides of the lens from below to hold the lens on the advancement axis.

In addition, the present invention according to a second aspect of the invention is characterized by the afore-mentioned upper holding member that holds the lens by the edge.

In addition, the present invention according to a third aspect of the invention is characterized by the afore-mentioned upper holding member having a contact surface with the lens comprising an arc with a radius of curvature smaller than the lens optical area.

In addition, the present invention according to a fourth aspect of the invention is characterized by the afore-mentioned upper holding member having formed therein a insertion pass-through groove thorough which the afore-mentioned lens discharge mechanism passes parallel to the advancement axis.

In addition, the present invention according to a fifth aspect of the invention is characterized by the afore-mentioned lower holding member provided with a partition placed between the lens and the afore-mentioned lens discharge mechanism and a locking section having an insertion pass-through hole through which the afore-mentioned lens discharge mechanism passes.

The intraocular lens insertion device according to the first aspect of the present invention can push up the lower holding member while holding the lens in the advancement axis to fold into two the lens to eliminate the need to move the lens and allow the device to be made smaller.

In addition, the intraocular lens insertion device according to the second aspect is provided with an upper holding member that holds the edge of the lens such that the lens can be held without deforming the curved lens.

In addition, the intraocular lens insertion device according to the third aspect can prevent the contact surface of the upper holding member from contacting the optical area of the lens and can hold the lens without deforming the curved optical area, due to the curved shape of the contact surface viewed from the side.

In addition, the intraocular lens insertion device according to the fourth aspect is provided with an upper holding member formed with an insertion pass-through groove having a width nearly the same or larger than the outside shape of the lens discharge mechanism such that the lens discharge mechanism does not contact the upper holding member so that there is no interference with the lens discharge operation and the lens can be smoothly discharged even if the lens discharge mechanism is offset in the upward direction.

In addition, the intraocular lens insertion device according to the fifth aspect is provided with a lower holding member that can fold in two the lens using an upward pushing motion and that can unlock the plunger to perform the operation in a simpler manner. Further, the plunger is locked by the locking section to prevent operational mistakes.

DETAILED DESCRIPTION OF THE INVENTION

The following describes preferred embodiments of the present invention with reference to the drawings.

Figure 1:
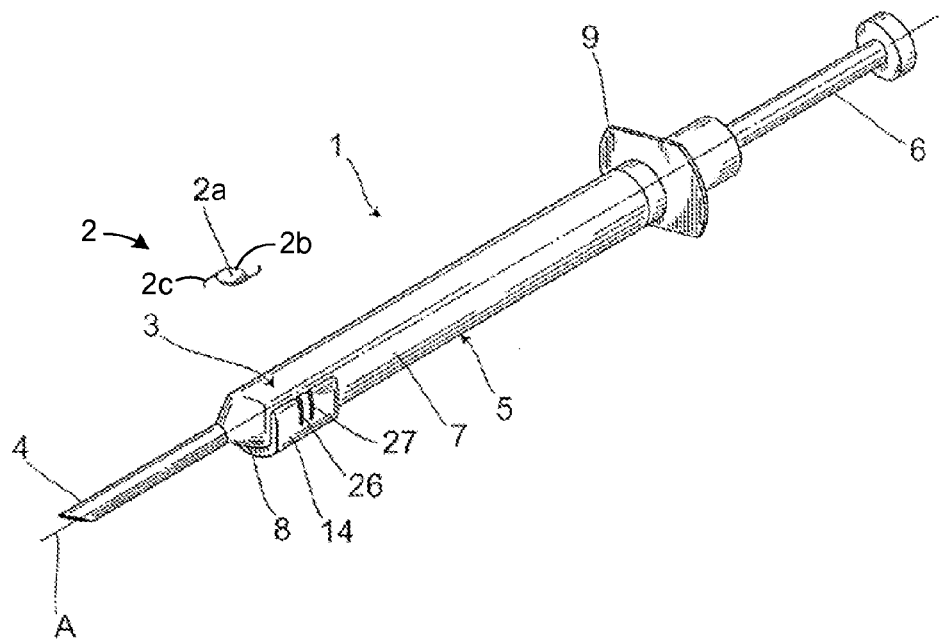
FIG. 1 is a complete oblique perspective view showing the construction of the intraocular lens insertion device according to an embodiment of the present invention.

The intraocular lens insertion device 1 shown in FIG. 1 is used to safely and quickly discharge into an eye a deformable intraocular lens 2 (hereinafter referred to as "lens 2"), and more particularly is a preset type intraocular lens insertion device 1 having a lens 2 preset in the intraocular lens insertion device 1. More specifically, the intraocular lens insertion device 1 is provided with a body 5 having a lens placement section 3 that holds the lens 2 and a tube section 4 that inserts the lens 2 into an eye, and a plunger 6 serving as a lens discharge mechanism that discharges the lens 2 that is placed in the afore-mentioned lens placement section 3.

The lens 2 used here may be made of a soft material, such as silicone resin, acrylic resin, or hydrogel. As illustrated in FIG. 1, the exemplary lens 2 has an optical area 2a, an edge region 2b that surrounds the optical area, and haptics 2c that extend outwardly from the edge region 2b.

The afore-mentioned body 5 is constructed of a tubular material and comprises the afore-mentioned tube section 4 whose end is cut off at an angle, a cylindrical section 7 formed with an outside shape that is wider than that of the afore-mentioned tube 4, and a tapered section 8 that joins the afore-mentioned tube section 4 and afore-mentioned cylindrical section 7. The afore-mentioned cylindrical section 7 comprises the lens placement section 3 that is placed on the end provided with the tube section 4. The proximal end of the afore-mentioned body 5 is provided with a flange 9 that protrudes in the radial direction of the body 5. Note that since the tube section 4 is inserted into the incision made in the eye ball, it must be made of a material that does not have a negative impact on the human body, such as polypropylene or other thermoplastic resin, for example.

The afore-mentioned body 5 is provided with a support member not shown in the figure that holds the plunger 6 in the position where the lens 2 can be discharged thereby and that supports the same in a manner capable of moving in the anteroposterior direction inside the body 5.

Figure 2:
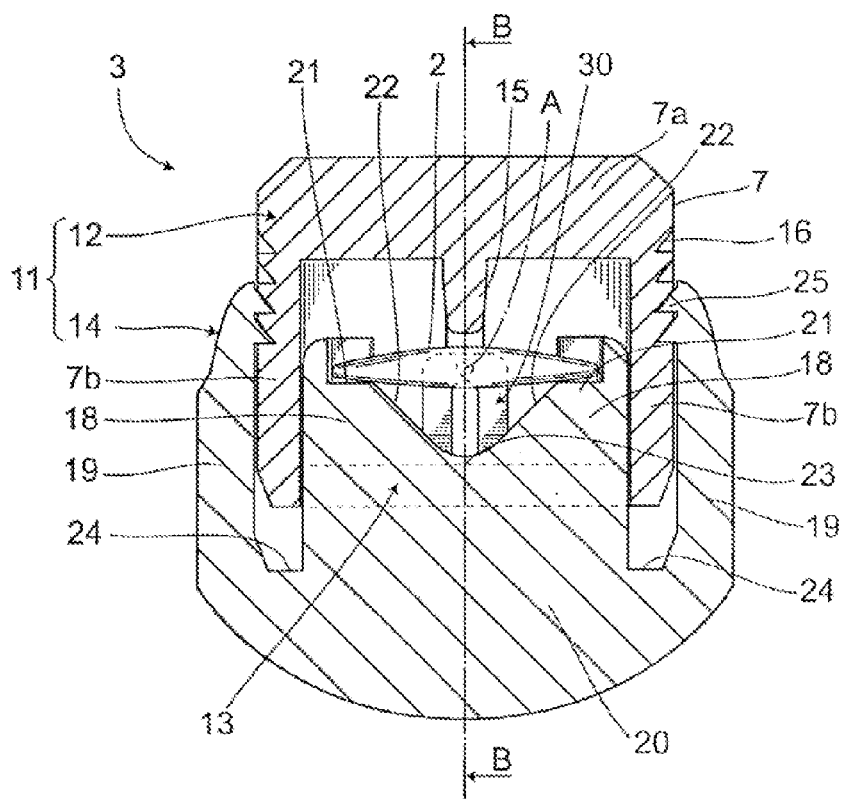
FIG. 2 is a vertical cross-section view of the construction of the lens placement section showing the holding state.

The afore-mentioned lens placement section 3 is provided with a deforming mechanism 11, and this deforming mechanism 11 is formed so as to be integrated with the body cylindrical section 7 and comprises an upper holding member 12 composed of a top plate 7a and side plates 7b of the body 5, and a lower holding material 14 that is mounted so as to cover an opening 13 that is formed in the bottom of the upper holding material 12 as shown in FIG. 2.

Figure 3:
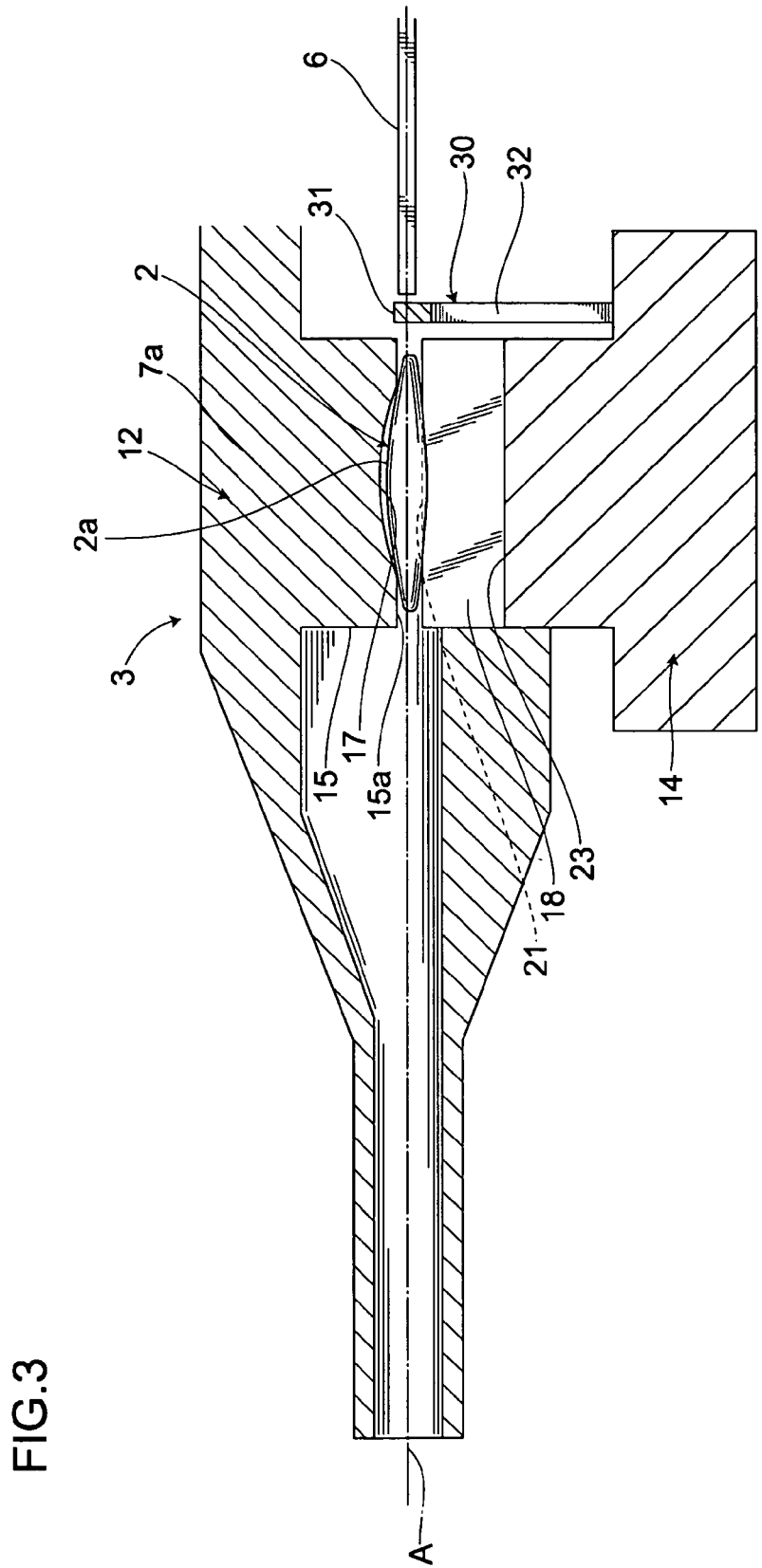
FIG. 3 is a cross-sectional view of FIG. 2 taken on a B-B line showing the holding state.

The afore-mentioned top plate 7a is provided with a rib 15 that protrudes downward in the direction of the afore-mentioned advancement axis A, and the afore-mentioned side plates 7b are provided with a concave engagement area 16 that engages with a hereafter-mentioned convex engagement area. The afore-mentioned rib 15 has a curved section 17 on a contact surface 15a that is curved upward as seen from the side, and this curved section 17 is formed by an arc having a radius of curvature that is smaller than that of the optical area of the lens 2 as shown in FIG. 3. Providing this curved section 17 makes it possible for the upper holding member 12 to hold the lens 2 by the edge of the lens 2.

As shown in FIG. 2, the afore-mentioned lower holding member 14 is formed by uprising sections 18 that protrude upward, and engagement sections 19 that engage from the outside of the afore-mentioned side plates 7b formed on the outside of the uprising sections 18, positioned on the right and left sides facing each other, and the afore-mentioned uprising sections 18 and the afore-mentioned engagement sections 19 are united into a single piece by a pressing section 20 at the bottom. The uprising sections 18, which are formed facing each other on the opposite sides left and right having the advancement axis A in the center consist of a placement surfaces 21, an inclined surfaces 22 that inclines downward towards the center, and an arc surface 23 that unites the inclined surfaces 22 at the center.

Between the afore-mentioned uprising sections 18 and engagement sections 19 is formed a groove section 24 into which is inserted the afore-mentioned side plate 7b. The afore-mentioned engagement sections 19 are provided with a protruding engagement section 25 that protrudes facing the body's side plate 7a, and the protruding engagement section 25 is provided on a movable member 27 cut with slits 26 (FIG. 1). The afore-mentioned protruding engagement section 25 and the concave engagement area 16 have a multiplicity of steps in the perpendicular direction to allow incremental positioning in the vertical direction of the lower holding member 14 in relation to the upper holding member 12 (FIG. 2).

Further, an uprising locking member 30 is formed as an up rise, constructed by a reverse U-shaped plate member on the base end side of the lower holding member 14. The locking member 30 comprises a partition 31 formed as an up rise on the rear end of the afore-mentioned pressing section 20 such that it intersects perpendicularly with the advancement axis A, and an insertion pass-through hole 32 that is formed in the approximate center of the bottom of the partition 31.

Next, the action of the afore-mentioned construction is explained. First, the lens 2 is placed in the lens placement section 3. More specifically, as shown in FIG. 2, the lens 2 is placed on the placement surface 21 in the lower holding member 14. The lower holding member 14 in which is placed the lens 2 allows the side plate 7b to be inserted into the groove section 24. When the side plate 7b is inserted into the groove section 24, the lower holding member 14 is further pushed up. When the lower holding member 14 is pushed up, the protruding engagement section 25 engages with the concave engagement section 16 and is mounted on the upper holding member 12. At this time, the lower holding member 14 is positioned by the protruding engagement section 25 such that the top of the lens 2 makes contact with the contact surface 15a of the rib 15.

In addition, as shown in FIG. 3, the contact surface 15a of the upper holding member 12 has the curved section 17 that prevents the contact surface 15a from making contact with the optical area of the lens 2 to hold the lens 2 without deforming the curved optical area. Further, the front and back edges of the contact surface 15a are formed to make contact with the lens 2 to hold the lens 2 while preventing the lens 2 from being displaced in the anteroposterior direction. In this manner, the lens 2 is held in place in the advancement axis A. More specifically, a part of the lens 2 is placed in the advancement axis A and held in a position where it can be discharged by the plunger 6. In this way, the positional relationship in the advancement axis A between the lens 2 and the plunger 6 is such that there is no change before and after deformation of the lens 2 in the lens placement section 3, which allows the plunger 6 to securely press against the specified area of the lens 2. Further, the plunger 6 is positioned to the rear of the lens 2 in the advancement axis A, but the placement of the locking member 30 between the lens 2 and the end of the plunger 6 impedes the forward movement of the plunger 6 to prevent the lens 2 from being mistakenly discharged. In addition, the protruding engagement section 25 formed in the uprising sections 18 engages with the concave engagement area 16 formed in the inside surface of the hole 24, mounted on the lens placement section, so that the lower holding member 14 prevents the lens 2 from being mistakenly folded into two during transport, etc., and, further, the locking member 30 locks the plunger 6 to prevent mistaken operation.

Figure 4:
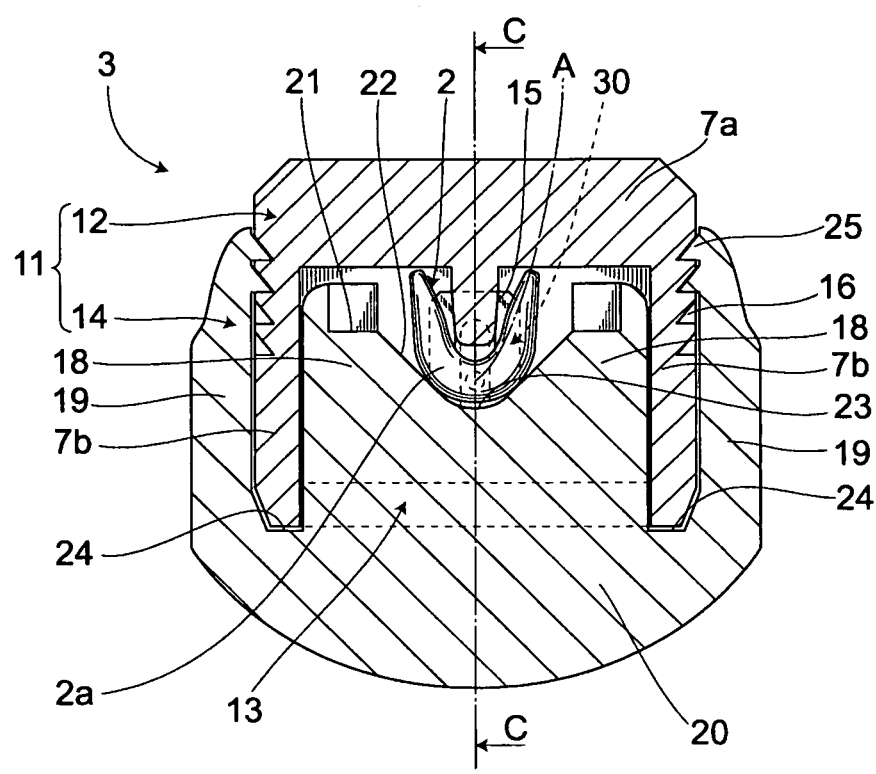
FIG. 4 is a vertical cross-section of the lens placement section showing the dischargeable state.

Next, the deforming of the lens 2 set in the lens placement section 3 is explained. As shown in FIG. 4, the afore-mentioned lower holding member 14 is pushed upwards. More specifically, when the pressing section 20 is pushed upwards, the engagement areas between the protruding engagement section 25 formed in the engagement sections 19 and the concave engagement areas 16 formed in the side plates 7b move upward. When the engagement areas between the protruding engagement section 25 and the concave engagement areas 16 move upward, the uprising sections 18 move upward. When the uprising sections 18 move upward, the inclined surfaces 22 make contact with the lens 2 and push up the lens 2. When the lens 2 is pushed up by the inclined surfaces 22, the center of the lens 2 is held from above by the rib 15 formed along the advancement axis A to fold into two the lens 2 in a U-shape. At this time, the afore-mentioned protruding engagement area is provided in the afore-mentioned movable member 27, so pushing up the lower holding member 14 elastically deforms the moveable member 27 in the outward direction to release the engagement and allow the engagement areas to easily move upward.

Figure 5:
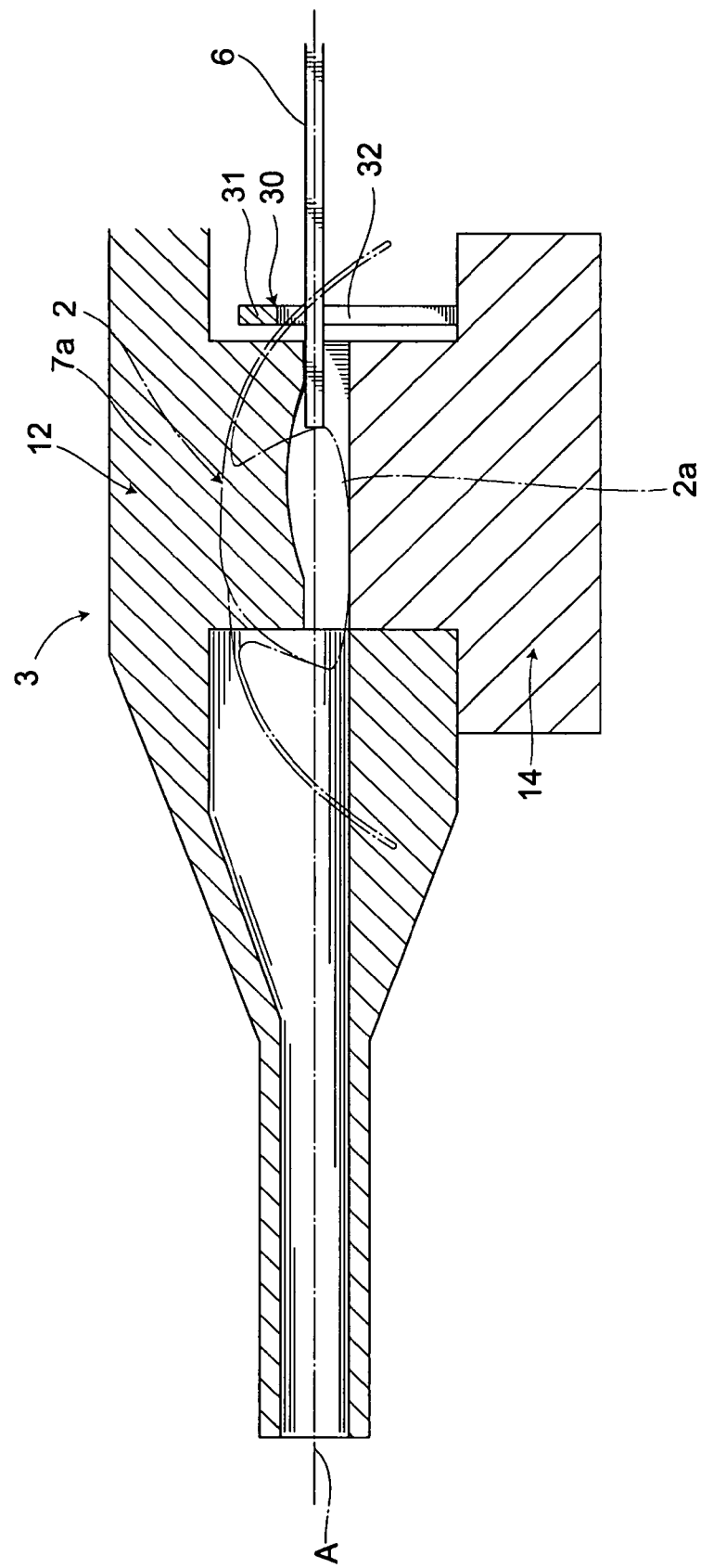
FIG. 5 is a cross-section of FIG. 4 taken on a C-C line showing the dischargeable state.

In addition, the upward movement of the engagement between the protruding engagement sections 25 and the concave engagement areas 16 moves the locking member 30 upwards as shown in FIG. 5. When the locking member 30 moves upward, the partition 31 that covers the end of the plunger 6 moves upward. When the partition 31 moves upward, the insertion pass-through hole 32 moves along the advancement axis A to release the lock of the plunger 6. In this way, the lens 2 is moved along the advancement axis A without being moved in the upward direction. More specifically, the lens 2 is folded into two by the plunger 6 while being held in a position where the lens 2 can be discharged, which allows the intraocular lens insertion device 1 to be made smaller and to eliminate problems that accompany the moving of the lens 2. Further, the lens 2 can be folded into two before it is discharged, so a shorter distance is required for the lens 2 to be discharged than when the lens 2 is incrementally deformed by passing it through the tapered section, which allows the body 5 to be made smaller. In addition, the upward pushing motion of the pressing section 20 can fold the lens 2 into two while also releasing the lock of the plunger 6 to allow the operation to be performed more simply.

Then, the lens 2, which has been folded into two, is discharged by the plunger 6, the lock of which has been released, and is inserted into the eye from the tube section 4. Since the fingers can hang onto the flange 9, the plunger 6 discharge operation can be done smoothly.

Figure 6:
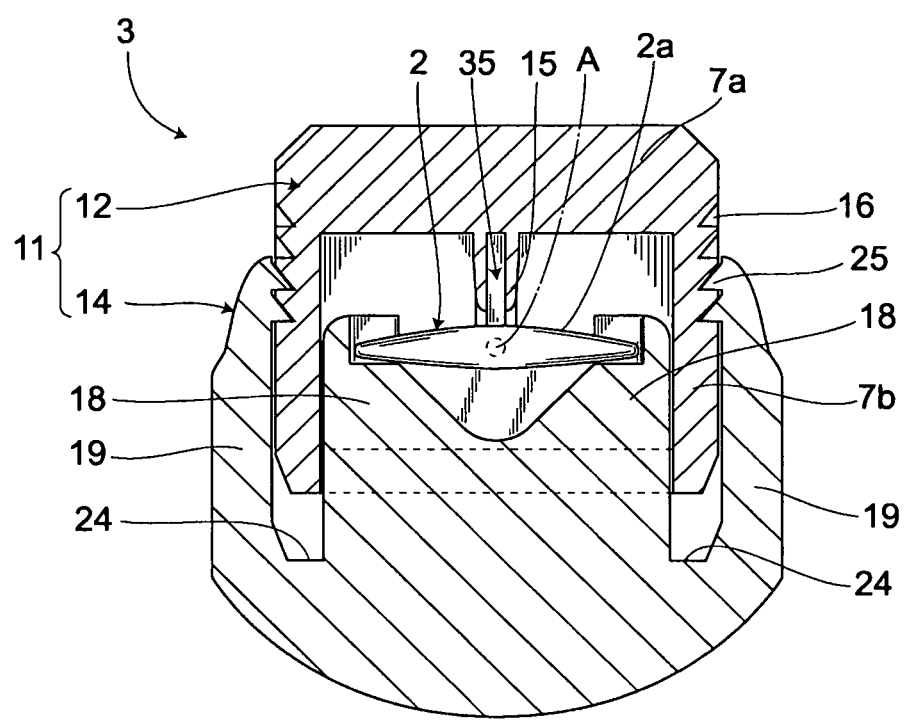
FIG. 6 is a vertical cross-section of a modified example of the lens placement section showing the holding state.

Next, a modified example of the afore-mentioned embodiment is explained making reference to FIG. 6. Note that when the configuration is the same as the afore-mentioned configuration, the same numbers are used and the explanation is omitted for simplification.

As shown in FIG. 5, the upper holding member 12 is formed with an insertion pass-through groove 35 that extends parallel to the advancement axis A in the center of the rib 15. This insertion pass-through groove 35 has the same or a slightly larger width than outside shape of the afore-mentioned plunger 6. In this manner, by forming the insertion pass-through groove 35 in the rib 15, the advancement of the plunger 6 when the plunger 6 discharges the lens 2 is not hindered by the rib 15. More specifically, even if the plunger 6 is off set in the upward direction, the rib 15 is formed with the insertion pass-through groove 35 having a width the same or slightly larger than the plunger 6, so the plunger 6 does not make contact with the rib 15. Therefore, the lens 2 can be smoothly discharged without the hindering of the operation that discharges the lens 2. Further, the rib 15 holds the center of the lens 2 along the advancement axis A, which makes it possible for the upward movement of the uprising sections 18 to fold the lens 2 into two.

As described above, this embodiment according to the first aspect is the intraocular lens insertion device 1 that is provided with the body 5 having the lens placement section 3 that holds the lens 2 and the tube section 4 that guides the lens 2 and the plunger 6 that is installed in the advancement axis A, wherein the afore-mentioned lens placement section 3 is provided with the deformation mechanism 11 comprising the upper holding member 12 that holds the lens 2 from above along the advancement axis A from back to front and the lower holding member 14 that holds the lens 2 from both sides to allow it to be pushed up from below, and by holding the lens 2 in the advancement axis A, it is possible to maintain the lens 2 in the advancement axis A while pushing up the lower holding member 14 to fold the lens 2 into two, so it is not necessary to move the lens 2, which allows the intraocular lens insertion device 1 to be made smaller.

In addition, according to the second aspect, the afore-mentioned upper holding member 12 holds the lens 2 by the edges of the lens to allow the lens 2 to be held without deforming the optical area 2a of the curved lens 2.

In addition, according to the third aspect, the afore-mentioned upper holding member 12 having the contact surface 15a with the lens 2 having the curved section 17 formed by an arc having a radius of curvature that is smaller than that of the optical area of the lens 2 whereby the contact area 15a is prevented from contacting the optical area of the lens 2, which allows the lens 2 to be held without deforming the curved optical area.

In addition, according to the fourth aspect, the afore-mentioned upper holding member 12 is formed with the insertion pass-through groove 35 through which passes the afore-mentioned plunger 6 in parallel to the advancement axis A, and the upper holding member 12 is formed with the insertion pass-through groove 35 having a width approximately the same or larger than that of the outside diameter of the plunger 6, which makes it so that the plunger 6 does not contact the upper holding member 12 even if the plunger 6 is off set in the upward direction. This allows the lens 2 to be smoothly discharged.

In addition, according to the fifth aspect, the afore-mentioned lower holding member 14 is provided with the locking member 30 comprising the partition 31 placed between the lens 2 and the afore-mentioned plunger 6 and the insertion pass-through hole 32 through which passes the afore-mentioned plunger 6 to make possible the performance of a simple operation that folds into two the lens 2 by the operation of pushing upward the lower holding member 14 while also unlocking the lock of the plunger 6. Further, the plunger 6 is locked by the locking member 30 to prevent mistaken operation.

The present invention is not limited by the foregoing embodiments and a variety of deformation embodiments within the intended scope of the present invention are possible.

The invention claimed is:

1. An intraocular lens insertion device for use with a lens having an optical axis, the intraocular lens insertion device comprising:
    a body having a lens placement section that holds the lens and a tube section that guides said lens, said lens defining a front portion that faces the tube section and a back portion that is spaced from and diametrically opposed to the front portion; and
    a lens discharge mechanism installed in an advancement axis, wherein said lens placement section is provided with a folding mechanism including
        an upper holding member that holds said lens by contacting the front and back portions of said lens from above along the advancement axis both prior to and after a folding caused by the folding mechanism, and
        a lower holding member that holds said lens from both sides to allow said lens to be pushed up from below while the lens is held on the advancement axis both prior to and after the folding,
        said upper holding member and said lower holding member being configured to fold said lens into a U-shape without movement of said lens along said lens advancement axis and such that the optical axis intersects the advancement axis both prior to and after the folding.

2. The intraocular lens insertion device according to claim 1, wherein
    said intraocular lens includes an optical area, an edge region that surrounds said optical area, and first and second haptics that extend outwardly from said edge region;
    said front and back portions comprise front and back portions of said edge region of said lens; and
    said upper holding member contacts the front and back portions of said edge region of said lens.

3. The intraocular lens insertion device according to claim 1, wherein
    said lens includes an optical area having a radius of curvature; and
    said upper holding member has a contact surface with a radius of curvature that is smaller than the radius of curvature of the optical area of said lens.

4. The intraocular lens insertion device according to claim 1, wherein said upper holding member is formed with an insertion pass-through groove through which said lens discharge mechanism passes in parallel to the advancement axis.

5. The intraocular lens insertion device according to claim 1, wherein said lower holding member is provided with a locking member comprising a partition placed between the lens and said lens discharge mechanism and an insertion pass-through hole through which said lens discharge mechanism passes.

6. The intraocular lens insertion device according to claim 1, wherein an optical area of said lens faces said upper holding member.

7. The intraocular lens insertion device according to claim 1, wherein the upper holding member is configured such that the upper holding member does not contact a portion of the lens between the front and back portions along the advancement axis when the upper holding member contacts the front and back portions prior to folding.

8. A method of storing an intraocular lens in an intraocular lens insertion device, the intraocular lens including an optical area with an optical axis, an edge region that surrounds the optical area, and first and second haptics that extend outwardly from the edge region, the intraocular lens insertion device including a lens storage section, a tube section, a plunger that moves through the lens storage section and the tube section along a lens advancement axis, and a lens deformation mechanism associated with the lens storage section, the method comprising the step of:
    prior to movement of the deformation mechanism, maintaining the position of the intraocular lens in an unstressed storage state within the lens storage section by contacting a first side of the intraocular lens with a first portion of the deformation mechanism at first and second first-side locations on the edge region that are spaced from one another along the lens advancement axis and by contacting a second side of the intraocular lens with a second portion of the deformation mechanism at first and second second-side locations that are spaced from one another in a direction transverse to the lens advancement axis and are offset from the first and second first-side locations about the intraocular lens optical axis.

9. A method as claimed in claim 8, wherein
    the first side of the intraocular lens comprises the top side; and
    the second side of the intraocular lens comprises the bottom side.

10. A method as claimed in claim 8, further comprising the step of:
    folding the intraocular lens by moving at least one of the first and second portions of the deformation mechanism relative to the other while the first side of the intraocular lens is contacted by the first portion of the deformation mechanism at the first and second first-side locations on the edge region and the second side of the intraocular lens is contacted the second portion of the deformation mechanism at the first and second second-side locations.

11. A method as claimed in claim 10, further comprising the step of:
    preventing the plunger from moving through the lens storage section with a portion of the deformation mechanism until after the deformation mechanism folds the intraocular lens.

12. A method as claimed in claim 8, wherein
    contacting a first side of the intraocular lens comprises contacting a first side of the intraocular lens with a first portion of the deformation mechanism at first and second first-side locations on the edge region that are spaced from one another along the lens advancement axis without contacting a portion of the first side of the intraocular lens between the first and second first-side locations.

13. An intraocular lens insertion device, comprising:
a lens storage section;
a tube section operably connected to the lens storage section;
a plunger, movable through the lens storage section and the tube section, and having a longitudinal axis that defines a lens advancement axis;
an intraocular lens located within the lens storage section at a lens storage position and on the lens advancement axis such that the intraocular lens defines front and back portions that are spaced from one another along the lens advancement axis and side portions that are spaced from one another in a direction transverse to the lens advancement axis; and
a deformation mechanism associated with the lens storage section and including first and second holding members that are movable relative to one another between a storage state, where the intraocular lens is at the lens storage position and unfolded and the lens advancement axis passes through the front and back portions, and a folded state, where the intraocular lens is at the lens storage position and is folded into a U-shape and the lens advancement axis passes through the front and back portions.

14. An intraocular lens insertion device as claimed in claim 13, wherein
the first holding member comprises an upper holding member that holds the intraocular lens by contacting the front and back portions of the intraocular lens both prior to and after a deformation caused by the deformation mechanism; and
the second holding member comprises a lower holding member that holds the intraocular lens from the sides portions both prior to and after the deformation caused by the deformation mechanism.

15. An intraocular lens insertion device as claimed in claim 14, wherein
the intraocular lens includes an optical area, an edge region that surrounds the optical area, and first and second haptics that extend outwardly from the edge region;
the front and back portions comprise front and back portions of the edge region of the intraocular lens; and
the upper holding member contacts the front and back portions of the edge region of the intraocular lens.

16. An intraocular lens insertion device as claimed in claim 14, wherein
the upper holding member is configured such that it does not contact a portion of the intraocular lens between the front and back portions of the intraocular lens.

17. An intraocular lens insertion device as claimed in claim 16, wherein
the intraocular lens includes an optical area having a radius of curvature; and
the upper holding member has a contact surface with a radius of curvature that is smaller than the radius of curvature of the optical area of the intraocular lens.

18. An intraocular lens insertion device as claimed in claim 13, wherein
the lens deforming mechanism is configured to prevent the plunger from moving through the lens storage section until after the deformation mechanism folds the intraocular lens.

19. The intraocular lens insertion device according to claim 1, wherein
said lens includes an optical area, an edge portion that surrounds said optical area, and first and second haptics that extend outwardly from said edge region; and
said upper holding member holds said lens by contacting front and back portions of said edge region of said lens from above.

20. An intraocular lens insertion device as claimed in claim 13, wherein
the lens includes an optical area, an edge region that surrounds the optical area, and first and second haptics that extend outwardly from the edge region; and
the first holding member contacts the front and back portions of the intraocular lens edge region both prior to and after a deformation caused by the deformation mechanism.

21. An intraocular lens insertion device as claimed in claim 13, wherein
the deformation mechanism is configured such that the intraocular lens is deformed during movement of the first and second holding members relative to one another.

22. An intraocular lens insertion device as claimed in claim 13, wherein
the deformation mechanism is configured such that the intraocular lens is deformed without movement of the intraocular lens along the lens advancement axis.

* * * * *